US00PP12162P2

(12) United States Plant Patent
Miyazaki

(10) Patent No.: US PP12,162 P2
(45) Date of Patent: Oct. 23, 2001

(54) SENECIO GENUS PLANT NAMED 'SUNSENERE'

(75) Inventor: Kiyoshi Miyazaki, Hikone (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/345,736

(22) Filed: Jul. 1, 1999

(51) Int. Cl.[7] ..... A01H 5/00
(52) U.S. Cl. ..... Plt./263
(58) Field of Search ..... Plt./263

(56) References Cited

PUBLICATIONS

Asteraceae Cadistics and Classification, Kare Bremer, 1994, Timber Press, Inc., p. 508.*

* cited by examiner

*Primary Examiner*—Bruce R. Campell
*Assistant Examiner*—Anne Marie Grünberg
(74) *Attorney, Agent, or Firm*—Burns, Doane, Swecker & Mathis, L.L.P.

(57) ABSTRACT

Disclosed herein is a Senecio genus plant named 'Sunsenere' being of a high height and dome-shaped plant with abundant branching. There are very few pubescences on its stems. Leaf length is shorter and petiole length is longer than in *Senecio L.* 'Sunsenere' has no stipule. It has large flower clusters. Flowers are single flowered and have no marginal variegation. The color of the petal is vivid reddish purple and the disk flower is deep reddish purple. Blooming period is early and blooming term is longer than *Senecio cruentus*. Flower buds grow one after another from axil. The novel characteristics of 'Sunsenere' include (A) being a high and dome-shaped plant with abundant branching, (B) having very few pubescences on its stems, (C) having short leaves and a long petiole, (D) having a large flower cluster, (E) having petals of vivid reddish purple, disk flowers of deep reddish purple, and flowers with no marginal variegation, (F) having a long blooming term and (G) having low fertility.

2 Drawing Sheets

BACKGROUND OF THE VARIETY

The present invention relates to a new and distinct variety of Senecio genus plant named 'Sunsenere'. 'Sunsenere' is a distinct and unique variety, which is a dome-shaped plant of high height with abundant branching, vivid reddish purple flowers, and a long blooming term.

There are many varieties in *Senecio L. Senecio cruentus* is well known as 'Cineraria' and cultivated in the world. There are many cultivated varieties with flowers of a single color of white, pink red, blue or violet. Some varieties have marginal variegation with off color parts.

The female parent used in the crossing of 'Sunsenere' is a cultivar, *Senecio cruentus*, 'Jupiter Crimson' (not patented in the United States), which is a compact, dome-shaped plant, 17 cm in height. The stems are thick, 8.5 mm in diameter, with anthocyanin coloration. The leaf is of a serrated heart form and moderate yellowish green. The leaf size is medium, 12.5 cm long and 13.5 cm wide. The flower is single flowered and has strong purplish red petals with moderate purplish red disk flowers having no marginal variegation. 'Jupiter Crimson' has some scent.

The pollen parent used in the crossing of 'Sunsenere' is *Senecio heritierii* (having no variety name; not patented or sold in the United States), which was introduced from nurseries in England. *Senecio heritierii* is a high and dome-shaped plant, 26 cm in height with abundant branching. The stems are 5.1 mm in diameter, with no anthocyanin coloration. The leaf is in a serrated heart form and light yellowish green. The leaf is small, 5.5 cm long and 6.3 cm wide. Flowers are single flowered, having strong purple petals with vague white parts and strong reddish purple disk flowers. *Senecio heritierii* has no scent.

The controlled crossing with *Senecio cruentus* 'Jupiter Crimson' and *Senecio heritierii* was first conducted at Hakusho-cho, Kitokoma-gun, Yamanashi-ken, Japan in January 1995. Seedlings from this crossing were grown since July 1995. The new variety was selected in January 1996 among them in view of flower color and early blooming. After multiplication by tissue culture, the botanical characteristics of the selected new variety were examined and tested in potting, using parent varieties and 'Miss Yokohama' and 'Midget' (both not patented in he United States) for comparison, since July 1996. As a result, it is confirmed that this selected variety met our criteria of being uniform and stable in its characteristics.

Then this new variety of Senecio genus plant was named 'Sunsenere' (*Senecio cruentus*×*Senecio heritierii*).

*Senecio cruentus*, 'Jupiter Crimson', and *Senecio heritierii* are presently maintained at the Hakusho-cho, Kitokoma-gun, Yamanashi-ken, Japan.

In the following descriptions, the color-coding is in accordance with the Horticultural Colour Chart of The Royal Horticultural Society, London, England (R.H.S. Colour Chart). In some instances, the color-coding based on color charts from The Japan Color Standard for Horticultural Plant (J.H.S. Color Chart) is also added for reference.

The botanical characteristics of the female parent plant *Senecio cruentus*, 'Jupiter Crimson', used in the crossing of 'Sunsenere' are as follows.

Plant:

*Growth habit.*—Dwarf compact.
*Height.*—17 cm.

Stem:
*Thickness.*—8.5 mm.
*Color.*—Moderate yellowish green (R.H.S.C.C.No. 139C, J.H.S.C.C.No. 3709).
*Anthocyanin coloration.*—Present.
*Degree of anthocyanin coloration.*—Medium.
*Branching.*—Abundant.
*Type of primary lateral shoot.*—Branch from every node.
*Pubescence.*—Sparse.
*Length of internode.*—0.5 cm.

Leaf:
*Whole shape.*—Heart form with a swollen basal part, which is notched at where the basal part of the blade attaches to the petiole.
*Depth of concavity of leaf margin.*—Shallow.
*Type of convexity.*—Acute.
*Apex shape.*—Obtuse.
*Base shape.*—Cordate.
*Degree of undulation.*—Fair.
*Length.*—12.5 cm.
*Width.*—13.5 cm.
*Diameter of petiole.*—5.5 mm.
*Length of petiole.*—5.7 cm.
*Stipule.*—Absent.
*Color of upper surface.*—Moderate yellow green (R.H.S.C.C.No. 137D, J.H.S.C.C.No. 3712).
*Color of reverse surface.*—Grayish yellow green (R.H.S.C.C.No. 138B, J.H.S.C.C.No. 3715).
*Anthocyanin coloration of reverse surface.*—Absent.
*Pubescence of upper surface.*—Present.
*Pubescence of reverse surface.*—Dense.
*Color of pubescence of reverse surface.*—White.

Flower (single flowered):
*Shape of flower cluster.*—Flat.
*Diameter of flower cluster.*—20 cm.
*Height of flower cluster.*—9 cm.
*Transected shape of corolla.*—Flat.
*Diameter of flower.*—6.5 cm.
*Size of disk flower.*—1.8 cm.
*Color of petal.*—Strong purplish red (R.H.S.C.C.No. 67A, J.H.S.C.C.No. 9708).
*Marginal variegation.*—Absent.
*Color of disk flower.*—Moderate purplish red (R.H.S.C.C.No. 64A, J.H.S.C.C.No. 9714).
*Petal length.*—2.4 cm.
*Petal width.*—1.1 cm.
*Shape of petal.*—Rectangular.
*Lengthwise warp of petal.*—Convex.
*Concavity of petal tip.*—Present.
*Shape of petal tip.*—Rounded.
*Number of ray flower.*—13.
*Number of disk flower.*—120.
*Diameter of pedicel of the first flower.*—1.8 mm.
*Length of pedicel of the first flower.*—2.5 cm.
*Number of flowers per a flower cluster.*—53.
*Scent.*—Present.

Calyx:
*Degree of concavity.*—Flat.
*Degree of recurvature.*—2.5 mm.
*Color.*—Moderate yellowish green (R.H.S.C.C.No. 139C, J.H.S.C.C.No. 3709).
*Anthocyanin coloration.*—Absent.

Pistil:
*Color.*—Moderate purplish red (R.H.S.C.C.No. 64A, J.H.S.C.C.No. 9714).
*Number.*—1.
*Type.*—Style branches truncate (i.e. the top of the style is separated into two and the shape of the top is truncated).

Stamen:
*Color.*—Moderate purplish red (R.H.S.C.C.No. 64A, J.H.S.C.C.No. 9714).
*Type.*—5 anthers are connate, with separated filaments.
*Blooming period.*—December (Sowing in August).

Hardiness:
*Cold.*—Good.
*Rain.*—Good.
*Heat.*—Good.

Resistance:
*Disease.*—Good.
*Insect.*—Good.

The botanical characteristics of the male parent plant *Senecio heritierii* used in the crossing of 'Sunsenere' are as follows.

Plant:
*Growth habit.*—Semi-dwarf erect.
*Height.*—26 cm.

Stem:
*Thickness.*—5.1 mm.
*Color.*—Very pale green (R.H.S.C.C.No. 128D, J.H.S.C.C.No. 4902).
*Anthocyanin coloration.*—Absent.
*Branching.*—Abundant.
*Type of primary lateral shoot.*—Branch from every node.
*Pubescence.*—Dense.
*Length of internode.*—0.8 cm.

Leaf:
*Whole shape.*—Heart form with a swollen basal part, which is notched at where the basal part of the blade attaches to the petiole.
*Depth of concavity of leaf margin.*—Medium.
*Type of convexity.*—Acute.
*Apex shape.*—Obtuse.
*Base shape.*—Cordate.
*Degree of undulation.*—Weak.
*Length.*—5.5 cm.
*Width.*—6.3 cm.
*Diameter of petiole.*—3.5 mm.
*Length of petiole.*—7.5 cm.
*Stipule.*—Absent.
*Color of upper surface.*—Light yellowish green (R.H.S.C.C.No. 136D, J.H.S.C.C.No. 4002).
*Color of reverse surface.*—Very pale green (R.H.S.C.C.No. 128D, J.H.S.C.C.No. 4902).
*Anthocyanin coloration of reverse surface.*—Absent.
*Pubescence of upper surface.*—Dense.
*Pubescence of reverse surface.*—Dense.
*Color of pubescence of reverse surface.*—White.

Flower (single flowered):
*Shape of flower cluster.*—Uneven.
*Diameter of flower cluster.*—18 cm.
*Height of flower cluster.*—15 cm.
*Transected shape of corolla.*—Flat.
*Diameter of flower.*—4.8 cm.
*Size of disk flower.*—0.9 cm.
*Color of petal.*—Strong purple (R.H.S.C.C.No. 81B, J.H.S.C.C.No. 8605).
*Marginal variegation.*—Present.

*Diameter of off color part.*—1.3 cm.
*Border of marginal variegation.*—Vague.
*Color of disk flower.*—Strong reddish purple (R.H.S.C.C.No. 72A, J.H.S.C.C.No. 9214).
*Petal length.*—2.2 cm.
*Petal width.*—0.4 cm.
*Shape of petal.*—Rectangular.
*Lengthwise warp of petal.*—Flat.
*Concavity of petal tip.*—Present.
*Shape of petal tip.*—Acute.
*Number of ray flower.*—13.
*Number of disk flower.*—110.
*Diameter of pedicel of the first flower.*—1.2 mm.
*Length of pedicel of the first flower.*—2.5 cm.
*Number of flowers per a flower cluster.*—35.
*Scent.*—Absent.

Calyx:
*Degree of concavity.*—Flat.
*Degree of recurvature.*—3.1 mm.
*Color.*—Very pale green (R.H.S.C.C.No. 128D, J.H.S.C.C.No. 4902).
*Anthocyanin coloration.*—Present.

Pistil:
*Color.*—Strong reddish purple (R.H.S.C.C.No. 72A, J.H.S.C.C.No. 9214).
*Number.*—1.
*Type.*—Style branches truncate (i.e. the top of the style is separated into two and the shape of the top is truncated).

Stamen:
*Color.*—Strong reddish purple (R.H.S.C.C.No. 72A, J.H.S.C.C.No. 9214).
*Type.*—5 anthers are connate, with separated filaments.
*Blooming period.*—End of January (Sowing in August).

Hardiness:
*Cold.*—Good.
*Rain.*—Good.
*Heat.*—Good.

Resistance:
*Disease.*—Good.
*Insect.*—Good.

The botanical characteristics of a similar variety 'Miss Yokohama' used for examination as a comparison variety are as follows.

Plant:
*Growth habit.*—Dwarf compact.
*Height.*—19 cm.
*Spread.*—19 cm.

Stem:
*Thickness.*—5.4 mm.

Color: Moderate yellow green (R.H.S.C.C.No. 139C, J.H.S.C.C.No. 3709).
*Anthocyanin coloration.*—Present.
*Degree of anthocyanin coloration.*—Medium.
*Branching.*—Fair.
*Type of primary lateral shoot.*—Branch from every node.
*Pubescence.*—Dense.
*Length of internode.*—0.5 cm.

Leaf:
*Whole shape.*—Heart form with a swollen basal part, which is notched at where the basal part of the blade attaches to the petiole.
*Depth of concavity of leaf margin.*—Medium.
*Type of convexity.*—Acute.
*Size of wings.*—Large.
*Apex shape.*—Medium.
*Base shape.*—Cordate.
*Degree of undulation.*—Weak.
*Length.*—17.5 cm.
*Width.*—13.0 cm.
*Diameter of petiole.*—5.2 mm.
*Length of petiole.*—7.7 cm.
*Stipule.*—Present.
*Color of upper surface.*—Moderate yellow green (R.H.S.C.C.No. 137C, J.H.S.C.C.No. 3712).
*Color of reverse surface.*—Moderate yellow green (R.H.S.C.C.No. 138C, J.H.S.C.C.No. 3709).
*Anthocyanin coloration of reverse surface.*—Present.
*Degree of anthocyanin coloration.*—Medium.
*Pubescence of upper surface.*—Dense.
*Pubescence of reverse surface.*—Dense.
*Color of pubescence of reverse surface.*—White.

Flower (single flowered):
*Shape of flower cluster.*—Rounded.
*Diameter of flower cluster.*—23 cm.
*Height of flower cluster.*—17 cm.
*Transected shape of corolla.*—Flat.
*Diameter of flower.*—4.2 cm.
*Size of disk flower.*—1.1 cm.
*Color of petal.*—Vivid violet (R.H.S.C.C.No. 96A, J.H.S.C.C.No. 8005).
*Marginal variegation.*—Present.
*Diameter of off color part.*—2.5 cm.
*Border of marginal variegation.*—Fairly clear.
*Color of disk flower.*—Deep violet (R.H.S.C.C.No. 93A, J.H.S.C.C.No. 8006).
*Petal length.*—1.6 cm.
*Petal width.*—0.8 cm.
*Shape of petal.*—Rectangular.
*Lengthwise warp of petal.*—Convex.
*Concavity of petal tip.*—Present.
*Shape of petal tip.*—Rounded.
*Number of ray flower.*—13.
*Number of disk flower.*—86.
*Diameter of pedicel of the first flower.*—1.7 mm.
*Length of pedicel of the first flower.*—2.7 cm.
*Number of flowers per a flower cluster.*—90.
*Scent.*—Present.

Calyx:
*Degree of concavity.*—Flat.
*Degree of recurvature.*—1.2 mm.
*Color.*—Very pale green (R.H.S.C.C.No. 130D, J.H.S.C.C.No. 4302).
*Anthocyanin coloration.*—Absence.

Pistil:
*Color.*—Deep violet (R.H.S.C.C.No. 93A, J.H.S.C.C.No. 8006).
*Number.*—1.
*Type.*—Style branches truncate (i.e. the top of the style is separated into two and the shape of the top is truncated).

Stamen:
*Color.*—Deep violet (R.H.S.C.C.No. 93A, J.H.S.C.C.No. 8006).
*Type.*—5 anthers are connate, with separated filaments.
*Blooming period.*—January (Sowing in August).

Hardiness:
*Cold.*—Good.
*Rain.*—Good.

*Heat.*—Good.
Resistance:
*Disease.*—Good.
*Insect.*—Good.

The botanical characteristics of a similar variety 'Midget' used for examination as a comparison variety are as follows.

Plant:
*Growth habit.*—Dwarf.
*Height.*—14 cm.
Stem:
*Thickness.*—5.6 mm.
*Color.*—Moderate yellow green (R.H.S.C.C.No. 139C, J.H.S.C.C.No. 3709).
*Anthocyanin coloration.*—Present.
*Degree of anthocyanin coloration.*—Medium.
*Branching.*—Fair.
*Type of primary lateral shoot.*—Branch from every node.
*Pubescence.*—Dense.
*Length of internode.*—0.5 cm.
Leaf:
*Whole shape.*—Heart form with a swollen basal part, which is notched at where the basal part of the blade attaches to the petiole.
*Depth of concavity of leaf margin.*—Medium.
*Type of convexity.*—Acute.
*Apex shape.*—Acute.
*Base shape.*—Cordate.
*Degree of undulation.*—Fair.
*Length.*—13.9 cm.
*Width.*—10.3 cm.
*Diameter of petiole.*—4.2 mm.
*Length of petiole.*—4.7 cm.
*Stipule.*—Present.
*Color of upper surface.*—Grayish yellow green (R.H.S.C.C.No. 138A, J.H.S.C.C.No. 3514).
*Color of reverse surface.*—Grayish yellow green (R.H.S.C.C.No. 138B, J.H.S.C.C.No. 3715).
*Anthocyanin coloration of reverse surface.*—Absent.
*Pubescence of upper surface.*—Present.
*Pubescence of reverse surface.*—Dense.
*Color of pubescence of reverse surface.*—White.
Flower (single flowered):
*Shape of flower cluster.*—Flat.
*Diameter of flower cluster.*—22 cm.
*Height of flower cluster.*—8 cm.
*Transected shape of corolla.*—Fairly closed.
*Diameter of flower.*—3.2 cm.
*Size of disk flower.*—0.8 cm.
*Color of petal.*—Vivid reddish purple (R.H.S.C.C.No. 74A, J.H.S.C.C.No. 9207).
*Marginal variegation.*—Absent.
*Color of disk flower.*—Strong reddish purple (R.H.S.C.C.No. 72A, J.H.S.C.C.No. 9209).
*Petal length.*—1.5 cm.
*Petal width.*—0.8 cm.
*Shape of petal.*—Elliptical.
*Lengthwise warp of petal.*—Flat.
*Concavity of petal tip.*—Present.
*Shape of petal tip.*—Acute.
*Number of ray flower.*—13.
*Number of disk flower.*—86.
*Diameter of pedicel of the first flower.*—1.5 mm.
*Length of pedicel of the first flower.*—2.5 cm.
*Number of flowers per a flower cluster.*—180.
*Scent.*—Present.
Calyx:
*Degree of concavity.*—Flat.
*Degree of recurvature.*—2.2 mm.
*Color.*—Moderate yellow green (R.H.S.C.C.No. 139C, J.H.S.C.C.No. 3709).
*Anthocyanin coloration.*—Absent.
Pistil:
*Color.*—Strong reddish purple (R.H.S.C.C.No. 72A, J.H.S.C.C.No. 9209).
*Number.*—1.
*Type.*—Style branches truncate (i.e. the top of the style is separated into two and the shape of the top is truncated).
Stamen:
*Color.*—Strong reddish purple (R.H.S.C.C.No. 72A, J.H.S.C.C.No. 9209).
*Type.*—5 anthers are connate, with separated filaments.
*Blooming period.*—January (Sowing in August).
Hardiness:
*Cold.*—Good.
*Rain.*—Good.
*Heat.*—Good.
Resistance:
*Disease.*—Good.
*Insect.*—Good.

SUMMARY OF THE VARIETY

'Sunsenere' is a dome-shaped plant of high height (average height of 25 cm in the blooming period). There is a branch from every node and branching is abundant, i.e. 9 to 11 branches. The stem is 5.0 mm in diameter with anthocyanin coloration and few pubescences.

The leaves are small, 8.6 cm long and 10.3 cm wide. The leaves are shaped in a serrated heart form with a swollen basal part, which is notched at where the basal part of the blade attaches to the petiole. The leaf color is moderate yellowish green, with no anthocyanin coloration on reverse side. Pubescence on both sides of leaf is dense. The petiole is 9.0 cm long and 3.2 mm in diameter.

The new variety has large flower clusters which are high and uneven in shape (i.e. the locations of the individual flowers forming the cluster are uneven or not flat). A flower cluster means a gathering of heads in a plant of the new variety. A head is a flower consisting of a disk and a plurality of petals, i.e. ray flowers. The flower is single flowered with no marginal variegation. The corolla has a flat transected shape (i.e. when the corolla opens, petals are flat when viewed from the side). The flower is 6.4 cm in diameter, while the disk flower is 1.3 cm in diameter. The petal is 2.6 cm long and 0.8 cm wide. Before blooming, the color of the petal is vivid reddish purple (R.H.S.C.C. No. 74A), while the color of the disk is deep reddish purple (R.H.S.C.C. No. 71B). One flower has 15–16 ray flowers and 130 disk flowers. A ray flower has a pistil and a stamen formed by 5 connate anthers with separated filaments. A disk flower is tubular and has a pistil, but no stamen. 88 flowers are in a flower cluster. The degree of recurvature of calyx is 1.2 mm. The calyx is flat and has no anthocyanin coloration. Pedicel is 3.3 cm long and 1.2 mm in diameter. The flowers have some scent.

Blooming period is early and blooming term is long. After cutting in July, flowers begin to bloom at the end of November or in the first 10 days of December in Hakushucho, Kitakomer-gun, Yamanashi-ken, Japan. The blooming continues from December to May, if under appropriate control. Around a temperature of 15° C., the individual bloom lasts 2 weeks. The flower buds grow one after another from the axil. The flower is not self-cleaning because petals remain attached in a wilted and dry state as the flower fully matures.

The new variety has moderate cold hardiness and resistance to heat. The new variety does not die at aroung 0° C., but when frost occurs the cells can be necrosed resulting in the death of the plant. Usually, *Senecio cruentus* has a tendency of slightly reduced growth in a hot season, whereas the new variety has no problem in growing in the hot season.

The fertility of the new variety is low. Generally, Senecio genus plants have high fertility (i.e. bear many seeds per flower). In contrast, 'Sunsenere' bears no seed or very few seeds per flower. When no seed is formed, there is a part corresponding to a seed coat, which remains in an immature state, i.e. without embryo and endosperm inside the immature seed coat.

The new variety, 'Sunsenere', differs from similar varieties, 'Miss Yokohama' and 'Midget', of the Senecio genus and from parent varieties *Senecio heritierii* and 'Juptier Crimson' in the following points.

1. 'Sunsenere' is a high type plant, 25 cm in height. 'Miss Yokohama' is a compact type plant, 19 cm in height. 'Midget' is a compact type. plant, 14 cm in height. The pollen parent *Senecio heritierii* is a semi-compact type plant, 26 cm in height and female parent 'Jupiter Crimson' is a compact type plant, 17 cm in height.

2. The flower of 'Sunsenere' has vivid reddish purple petals, deep reddish purple disk flowers and no marginal variegation. That of 'Miss Yokohama' has vivid violet petals, deep violet disk flowers and white marginal part. That of 'Midget' has vivid reddish purple petals, strong reddish purple disk flowers and no marginal variegation. That of female parent 'Jupiter Crimson' has strong purplish red petals, moderate purplish red disk flowers and no marginal variegation. That of pollen parent *Senecio heritierii* has strong purple petals, strong reddish purple disk flower and white marginal part.

3. The leaves of 'Sunsenere' are shorter than that of 'Miss Yokohama' or 'Midget'. The petiole length of 'Sunsenere' is longer than that of 'Miss Yokohama' or 'Midget'.

4. 'Sunsenere' has fewer pubescence of stems than that of 'Miss Yokohama' or 'Midget'.

5. The blooming term of 'Sunsenere' is longer than that of 'Miss Yokohama' or 'Midget'.

6. The fertility of 'Sunsenere' is lower than that of 'Miss Yokohama' or 'Midget'.

The plant height, flower color and leaf size are most distinctive characteristics of this new variety, 'Sunsenere'.

DESCRIPTION OF THE NEW VARIETY

Figure 1:
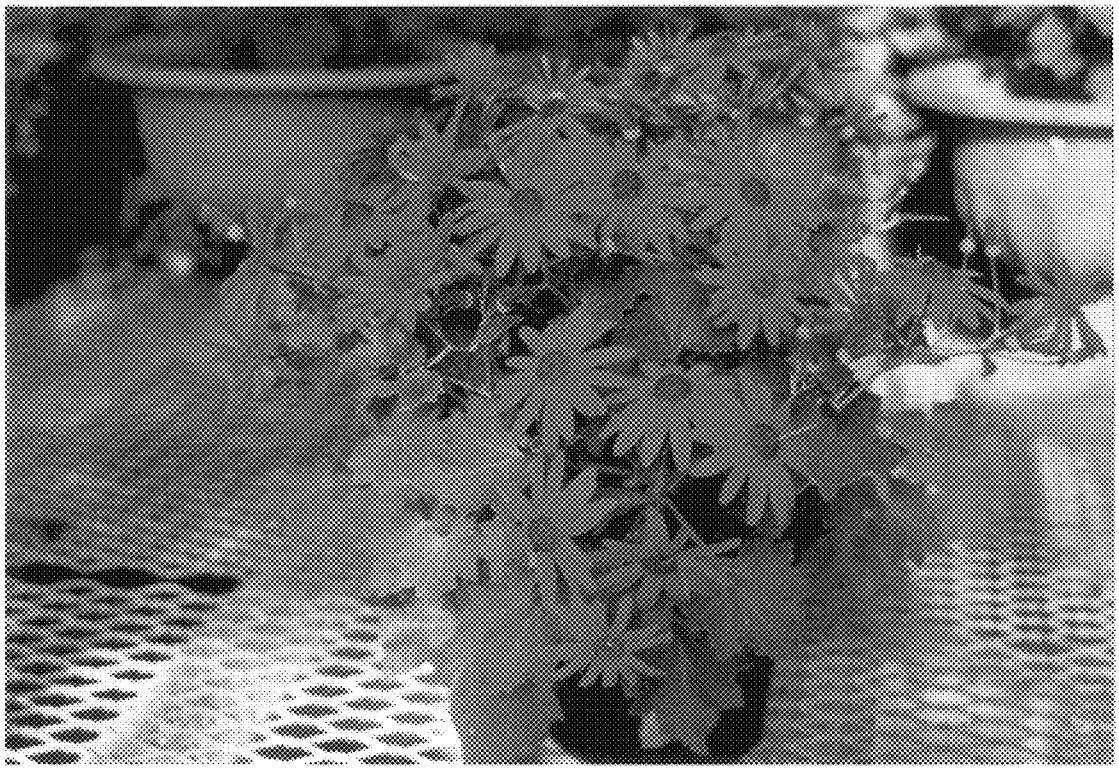
FIG. 1 is a photograph giving a partial view of the new variety of Senecio genus plant named 'Sunsenere' planted in a pot.
Figure 2:
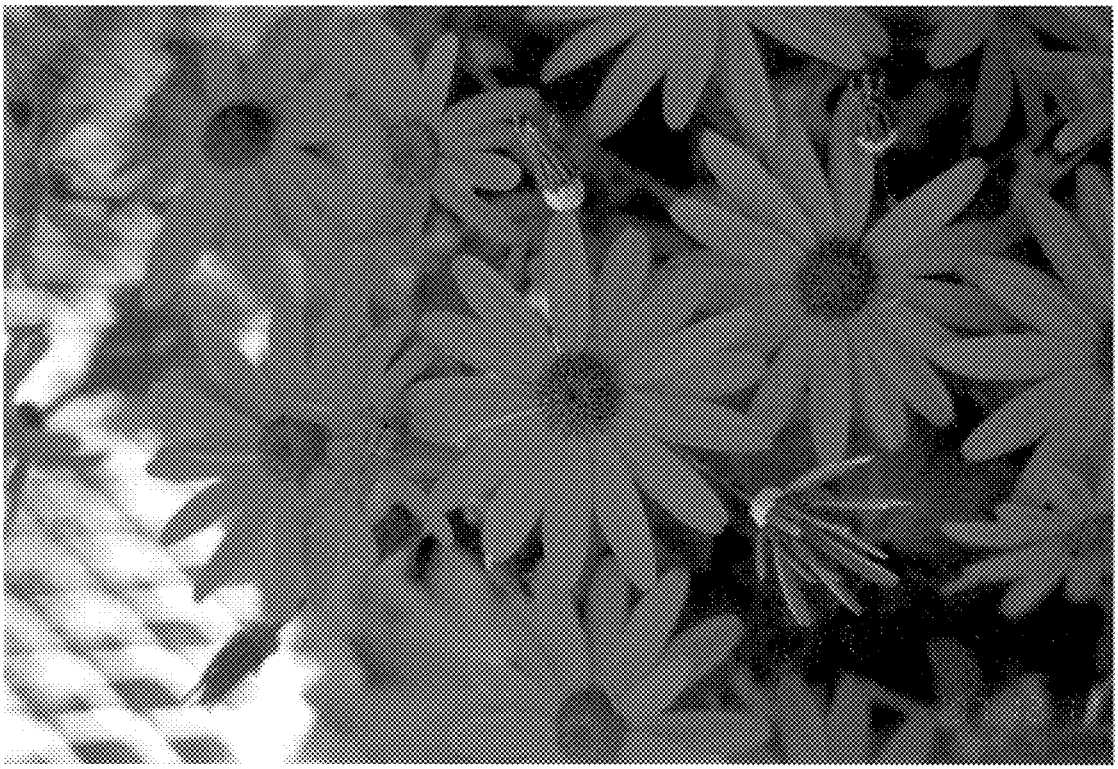
FIG. 2 is a photograph of flowers of the new variety of Senecio genus plant named 'Sunsenere'.

The botanical characteristics of this new and distinct variety of Senecio genus plant named 'Sunsenere' 6 months after cutting in July are as follows (i.e. these botanical characteristics were observed in January of the year following the cutting with the new variety planted in a 15 cm pot and grown in a green house, the lowest temperature of which was controlled at 12° C. in winter.

Plant:
- *Growth habit.*—Semi-dwarf erect.
- *Height.*—25 cm.

Stem:
- *Thickness.*—5.0 mm.
- *Color.*—Very pale green (R.H.S.C.C.No. 130D, J.H.S.C.C.No. 4302).
- *Anthocyanin coloration.*—Present in parts of the stem, e.g. can be seen at the part of peduncle.
- *Degree of anthocyanin coloration.*—It is light grayish olive (R.H.S.C.C. No. 197A) at the part wherein anthocyanin is present, but it is moderate yellowish green (R.H.S.C.C. No. 138C) at the part where anthocyanin is absent.
- *Branching.*—Abundant, i.e. 9 to 11 branches.
- *Type of primary lateral shoot.*—Branch from every node.
- *Pubescence.*—Sparse.
- *Length of internode.*—1.0 cm.

Leaf:
- *Whole shape.*—Heart form with a swollen basal part, which is notched at where the basal part of the blade attaches to the petiole.
- *Depth of concavity of leaf margin.*—The maximum depth of concavity measured from the average convexity peak height is 7 mm.
- *Leaf margin.*—Dentate with a pointed type of convexity.
- *Apex shape.*—Acute.
- *Base shape.*—Cordate.
- *Degree of undulation.*—Weak.
- *Length.*—8.6 cm.
- *Width.*—10.3 cm.
- *Diameter of petiole.*—3.2 mm.
- *Length of petiole.*—9.0 cm.
- *Color of petiole.*—R.H.S.C.C. No. 59B at the base (the side of a stem); R.H.S.C.C. No. 138B at the end (the side near the blade).
- *Stipule.*—Absent.
- *Color of upper surface.*—Moderate yellow green (R.H.S.C.C.No. 137C, J.H.S.C.C.No. 3712).
- *Color of reverse surface.*—Moderate yellow green (R.H.S.C.C.No. 138C, J.H.S.C.C.No. 3709).
- *Anthocyanin coloration of reverse surface.*—Absent.
- *Pubescence of upper surface.*—Dense.
- *Pubescence of reverse surface.*—Dense.
- *Color of pubescence of reverse surface.*—White.

Flower (single flowered):
- *Shape of flower cluster.*—Uneven.
- *Diameter of flower cluster.*—34 cm.
- *Height of flower cluster.*—22 cm (the height of the upper most flower in a flower cluster minus the height of the lowest flower in the same flower cluster is 22 cm).
- *Transected shape of corolla.*—Flat.
- *Diameter of flower.*—6.4 cm.
- *Size of disk flower.*—1.3 cm.
- *Color of petal.*—Vivid reddish purple (R.H.S.C.C.No. 78A, J.H.S.C.C.No. 8906).

*Marginal variegation.*—Absent (i.e. the petal coloration is consistent in the margin).
*Color of disk flower.*—Deep reddish purple (R.H.S.C.C.No. 80A, J.H.S.C.C.No. 8907).
*Petal length.*—2.6 cm.
*Petal width.*—0.8 cm.
*Shape of petal.*—Rectangular.
*Lengthwise warp of petal.*—Flat.
*Concavity of petal tip.*—Present.
*Shape of petal tip.*—Acute.
*Number of ray flower.*—15–16.
*Number of disk flower.*—130.
*Diameter of pedicel of the flower which blooms first and is attached to the top of the main stem.*—1.2 mm.
*Length of pedicel of the flower which blooms first and is attached to the top of the main stem.*—3.3 cm.
*Number of flowers per flower cluster.*—88.
*Scent.*—Present.

Calyx:
*Degree of concavity.*—Flat.
*Degree of recurvature.*—1.2 mm.
*Color.*—Very pale green (R.H.S.C.C.No. 130D, J.H.S.C.C.No. 4302).
*Anthocyanin coloration.*—Absent.

Pistil:
*Color.*—Vivid reddish purple (R.H.S.C.C.No. 80A, J.H.S.C.C.No. 8907).
*Number.*—1.
*Type.*—Style branches truncate (i.e. the top of the style is separated into two and the shape of the top is truncated).

Stamen:
*Color.*—Vivid reddish purple (R.H.S.C.C.No. 80A, J.H.S.C.C.No. 8907).
*Type.* —5 anthers are connate, with separated filaments.
*Blooming period.*—Begin at the end of November or early December (cutting in July).

Hardiness:
*Cold.*—Good.
*Heat.*—Good.

Resistance:
*Disease.*—Good (similar to *Senecio cruentus*).
*Insect.*—Good (similar to *Senecio cruentus*).

The new variety and *Senecio cruentus* have similar resistance to powdery mildew, leaf spot, aphid, whitefly and thrips. The new variety, 'Sunsenere', is a tall type plant and most suitable for flower potting.

This new and distinct variety of Senecio genus plant named 'Sunsenere' was asexually reproduced by cutting at Hakusho-cho, Kitokoma-gun, Yamanashi-ken, Japan and the homogeneity and stability thereof were confirmed.

I claim:

1. A new and distinct variety of Senecio genus plant named 'Sunsenere', substantially as herein illustrated and described.

* * * * *